United States Patent [19]

Rosenblatt et al.

[11] Patent Number: 4,681,739

[45] Date of Patent: * Jul. 21, 1987

[54] USE OF CHLORINE DIOXIDE GAS AS A CHEMOSTERILIZING AGENT

[75] Inventors: David H. Rosenblatt, Baltimore, Md.; Aaron A. Rosenblatt, New York, N.Y.; Joseph A. Knapp, Pittsburgh, Pa.

[73] Assignee: The Scopas Technology Co., Inc., New York, N.Y.

[*] Notice: The portion of the term of this patent subsequent to Mar. 12, 2002 has been disclaimed.

[21] Appl. No.: 601,443

[22] Filed: Apr. 18, 1984

Related U.S. Application Data

[63] Continuation-in-part of Ser. No. 435,331, Oct. 19, 1982, Pat. No. 4,504,442.

[51] Int. Cl.$^4$ ............................................. A61L 1/00
[52] U.S. Cl. ........................................ 422/37; 422/34; 423/477
[58] Field of Search ............... 422/34, 37; 423/477; 426/318, 320

[56] References Cited

U.S. PATENT DOCUMENTS

| | | | |
|---|---|---|---|
| 2,126,958 | 8/1938 | Guha | 99/154 |
| 2,394,064 | 2/1946 | Hutchinson | 99/192 |
| 2,409,084 | 10/1946 | Vincent | 127/71 |
| 2,482,958 | 9/1949 | Woodward | 426/318 |
| 2,546,568 | 3/1951 | Taylor | 426/318 X |
| 2,678,922 | 5/1954 | Stone | 252/187 |
| 2,691,637 | 10/1954 | Waibel | 252/187 |
| 2,701,781 | 2/1955 | Guevara | 167/17 |
| 2,903,367 | 9/1959 | Grindrod | 426/316 |
| 3,097,948 | 7/1963 | Ishikawa | 99/80 |
| 3,123,521 | 3/1964 | Wentworth et al. | 167/17 |
| 3,278,447 | 10/1966 | McNicholas | 252/187 |
| 3,591,515 | 7/1971 | Lovely | 252/187 |
| 3,687,612 | 8/1972 | Ernst | 422/34 X |
| 4,021,585 | 5/1977 | Svoboda | 426/332 |
| 4,066,399 | 1/1978 | Gunther | 422/34 X |
| 4,073,888 | 2/1978 | Snyder | 424/149 |
| 4,084,747 | 4/1978 | Alliger | 422/37 X |
| 4,104,190 | 8/1978 | Hartshorn | 252/187 |
| 4,194,622 | 3/1980 | Lewis | 422/34 X |
| 4,203,943 | 5/1980 | Gillis et al. | 422/34 X |
| 4,247,531 | 1/1981 | Hicks | 422/37 X |
| 4,284,653 | 8/1981 | Shigeoka et al. | 426/312 |
| 4,294,804 | 10/1981 | Baran | 422/34 X |
| 4,370,305 | 1/1983 | Affonso | 422/37 X |
| 4,504,442 | 3/1985 | Rosenblatt et al. | 422/37 |

FOREIGN PATENT DOCUMENTS

| | | |
|---|---|---|
| 263760 | 1/1928 | United Kingdom . |
| 1318996 | 5/1973 | United Kingdom . |

OTHER PUBLICATIONS

Chem. Ab. 94:78269e, Spotts et al., Chlorine and Chlorine Dioxide for Control of d'Anjou Pear Decay.
Chem. Ab. 94:176966z Conkey, Sporicidal Activities of Chlorine, Chlorine Dioxide and Peracetic Acid in a Simulated Papermaking Furnish.
Chem. Ab. 88:141730s Snyder, Chlorine Dioxide and Quaternary Ammonium Salts as Sterilizing Agents.
Benarde et al., Efficiency of Chlorine Dioxide as a Bactericide, Sep. 1965, 776-780, Applied Microbiology, 13.
Rosenblatt et al., The Reaction of Chlorine Dixode with Triethylamine in Aqueous Solution, Jan. 1963, 2790-2794, Joc 28.
Wheeler et al., A Rapid Microdetermination of Chlorine Dioxide in the Presence of Active Chlorine Compounds, Jun. 1978, 160-164, Microchemical Journal, 23.
"Sporicidal Properties of Chlorine Dioxide", Ridenour et al.; Water & Sewage Works; vol. 96, No. 8; Aug. 1948; pp. 279-283.
"Antiseptics, Disinfectants, Fungicides and Chemical and Physical Sterilization"; Reddish, George F.; 1957; p. 752.
M. M. Beeby and C. E. Whitehouse, A Bacterial Spore Test Piece for the Control of Ethylene Oxide Sterilization, *J. Appl. Bact.*, 28 349 (1965).
P. M. Borick, The Spore Problem, in *Disinfection*, M. A. Benarde, ed., Marcel Decker, Pub., N.Y. (1970) at pp. 85-102.
W. J. Masschelein, in *Chlorine Dioxide, Chemistry and Environmental Impact of Oxychlorine Compounds*, R. G. Rice, ed., Ann Arbor Sci. Pub. (1979) pp. 5-7, 152-183.
C. E. Gutch, et al., Failure of Dialysis Concentrate as a Bactericidal Agent, Proc. Dialysis Transplant Forum, 234 (1974).
R. P. Orcutt et al., Alcide: An Alternative Sterilant to Peracetic Acid, in Recent Advances in Germfree Research, S. Sasaki, ed., Tokai U. Press (c) 1981 at pp. 79-81.
Abdel-Rahman et al., Toxicity of Alcide, J. Appl. Tox., 2, 160 (1982).

Primary Examiner—Barry S. Richman
Assistant Examiner—William R. Johnson

[57] ABSTRACT

A method for sterilizing a substantially gas impermeable surface which is contaminated with spores comprises the steps of exposing the surface to a humid gaseous environment to enhance the susceptibility of the spores to subsequent chemosterilization, and then exposing the spores to an amount of gaseous chlorine dioxide in an inert carrier gas effective to sterilize the surface and a method for sterilizing an article contaminated with spores which comprises exposing the surface to a gaseous atmosphere comprised of chlorine dioxide gas and water vapor, wherein the amount of water vapor in said atmosphere is adapted to enhance the susceptibility of said spores to the sporicidal action of chlorine dioxide.

60 Claims, No Drawings

USE OF CHLORINE DIOXIDE GAS AS A CHEMOSTERILIZING AGENT

CROSS-REFERENCE TO RELATED APPLICATIONS

This application is a continuation-in-part of Ser. No. 435,331, filed Oct. 19, 1982, now U.S. Pat. No. 4,504,442, issued Mar. 12, 1985.

BACKGROUND OF THE INVENTION

The continuous introduction into technical use of new materials which cannot be radiation or heat sterilized or sterilized by exposure to liquid systems has necessitated the development of other means of sterilization. A major modern method for this purpose is based on the use of gaseous chemical agents. Such chemical compounds must be employed selectively, however, as only those which kill spores can be classified as chemical sterilizing agents. A wide variety of antimicrobial agents are available, but in most instances they do not kill resistant bacterial spores. Microbiocides are specifically limited to the destruction of the type of organism suffixed by "cide", e.g., bactericide refers to killing of bacteria, fungicide to fungi, viricide to viruses and sporicide to spores, both bacterial and fungal. Since bacterial spores are generally the most difficult to destroy, only sporicides may be considered synonymous with chemosterilizers. These may be defined as chemical agents which, when utilized properly, can destroy all forms of microbiological life, including bacterial and fungal spores and viruses.

Gaseous ethylene oxide and formaldehyde are used at many hospitals and medical research facilities to sterilize equipment or work areas that cannot be readily heat- or liquid-sterilized. Formaldehyde, if applied in high concentrations, is likely to leave a residue of solid paraformaldehyde. For this reason, it is often avoided in the sterilization of delicate equipment or in situations in which allergic reactions to this substance may occur. Ethylene oxide, which, unlike formaldehyde, penetrates well into porous materials, is strongly absorbed by rubber and by many plastics so that the vapors are not readily eliminated by brief aeration.

The publication of research relating to the mutagenicity and oncogenicity of both ethylene oxide and formaldehyde threatens to lead to severe limitations, if not outright bans, on the use of these compounds as sterilizing agents. The limitations would significantly increase the costs associated with ethylene oxide and formaldehyde sterilization.

Apart from its potential health hazards, ethylene oxide is difficult to handle at the concentrations and temperatures required for effective sterilization. Ethylene oxide at a 3–80% concentration in air is violently explosive and so ethylene oxide is commonly employed in admixture with an inert gas such as a fluorocarbon, for example, 12% ethylene oxide and 88% Freon 12 (E.I. duPont Co.). In the sterilization of medical products, temperatures as high as 130°–140° F. are commonly employed to ensure sterility at chamber concentrations of 300–1200 mg/L (milligrams per liter) of ethylene oxide. Prehumidification followed by gas exposure times of at least 4.0 hours are commonly employed. Also, ethylene oxide is more effective in killing dry spores on porous materials, such as paper or fabrics, than on nonporous materials such as glass, ceramics, hard plastics and metals. See C. W. Bruch and M. K. Bruch, *Gaseous Disinfection*, in *Disinfection*, M. A. Benarde, Ed., Marcel Decker, Pub., New York (1970) at pages 149–207.

Chlorine dioxide has long been recognized as being biologically active and early studies indicate that it possesses bactericidal, viricidal and sporicidal properties when applied in aqueous solution at minimum concentrations of about 0.20–0.25 mg/L. See W. J. Masschelein in *Chlorine Dioxide: Chemistry and Environmental Impact of Oxychlorine Compounds*, R. C. Rice, ed., Ann Arbor Science Pub. (1979); G. M. Ridenour, et al., Water & Sewage Works, 96, 279 (1949). However, more recent patents have stated that aqueous chlorine dioxide alone is not sporicidal unless used in the presence of stabilizers and/or activators. See Synder, U.S. Pat. No. 4,073,888. Sterilization with aqueous chlorine dioxide suffers from all of the general disadvantages associated with the use of aqueous sterilizing agents, including formulation and handling difficulties, the inability to sterilize moisture-sensitive equipment or substances, and the deposition of residues upon drying.

Little is known of the gas-phase chemistry of chlorine dioxide in air. At concentrations above about 10% (i.e., at about 300 mg per liter), the compound is unstable and sometimes detonates—probably in a shock or light-catalyzed decomposition. For this reason, chlorine dioxide gas cannot be stored. At the same concentration by weight in aqueous solution, it is quite stable.

The chemistry of chlorine dioxide in water is thought to be influenced by the formation of hydrates. At low temperatures (near 0° C.), high concentrations of chlorine dioxide precipitate out as hydrates of somewhat variable composition; warming permits these to redissolve. It is likely that chlorine dioxide in these warmed solutions still has some water molecules clustered about it. Such hydrates would not, of course, occur in the vapor phase.

In general, both the distance of molecules from one another in the gas phase and the absence of polar solvent effects must profoundly alter the chemistry of chlorine dioxide in air. Finally, not many large molecules have sufficient vapor pressure to co-exist with chlorine dioxide gas. Thus, compounds frequently available for reaction in natural water (e.g., proteins, certain amino acids, fumic acids and fulvic acids as well as most stabilizers) would not be found in the vapor state.

Lovely (U.S. Pat. No. 3,591,515) discloses powdered compositions which may be formulated to release 10–10,000 ppm of chlorine dioxide gas. The liberated chlorine dioxide gas is disclosed to be useful to kill bacteria and prevent fungus growth on fruit during shipment.

Due to the handling difficulties associated with chlorine dioxide, the differences in its gas phase and solution chemistry, and the inconsistencies in the above-cited work, chlorine dioxide gas has not been demonstrated to possess utility as a chemosterilizing agent at any concentration.

Accordingly, it is an object of the present invention to utilize chlorine dioxide gas as a chemosterilizing agent, i.e., as a sporicide, for a variety of materials commonly used for medical and dental implements and products.

It is another object of the present invention to utilize chlorine dioxide gas as a chemosterilizer at short exposure times and at near ambient temperature and near ambient pressures.

It is a further object of this invention to provide a method for sterilizing surfaces contaminated with spores by subjecting the surface to an atmosphere of controlled humidity either concurrently with or prior to application to the surface of sporicidal amounts of chlorine dioxide gas.

It is another object of the present invention to utilize chlorine dioxide as a chemosterilizing agent for materials such as medical implements which are sealed within gas permeable wrappings.

It is a further object of the present invention to utilize chlorine dioxide gas as a chemosterilizer for impermeable surfaces, which may be dried prior to sterilization.

Other objects, advantages and novel features of the present invention will be apparent to those skilled in the art from the following description and appended claims.

DETAILED DESCRIPTION OF THE INVENTION

This invention provides a method for sterilizing microbiologically contaminated articles, such as the dry and gas impermeable surfaces of medical or dental implements or other articles contaminated with live bacteria and bacterial spores.

The sterilant employed in the method described herein is gaseous chlorine dioxide, which is preferably employed in the form of a gaseous mixture of the chlorine dioxide in an inert carrier gas. A preferred inert carrier gas is nitrogen. In general, the concentration of chlorine dioxide sterilant in the inert carrier gas (e.g. nitrogen) may range from about 1.0 mg/L (milligrams per liter) to about 300 mq/L, preferably from about 8 mq/L to about 100 mg/L, and most preferably from about 10 mg/L to about 40 mg/L. As will be described in greater detail below, the particular concentration of chlorine dioxide in the carrier gas selected for use will be a function of several factors, including the inherent ability of the particular spores or live bacteria to resist the action of the sterilant, as well as the exposure time, and humidity conditions under which the object to be sterilized is contacted with the gaseous sterilant.

The relative humidity (RH) of an indoor environment rarely rises above about 60%, and is often below about 25% RH. Bacterial spores present on an essentially moisture-free substrate and exposed to low indoor ambient humidities will be in a low moisture or desiccated state. It is well recognized in the art that desiccated spores possess a high degree of resistance to chemical sterilizing agents. Thus, surfaces contaminated with desiccated spores will require substantially more rigorous sterilization conditions (e.g. higher sterilant concentration, longer exposure times, etc.), than would be required to sterilize the same type of spore in a non-desiccated state.

In accordance with an embodiment of this invention, the susceptibility of desiccated spores to chemosterilization with chlorine dioxide gas is enhanced by exposing the spores to a gaseous atmosphere of controlled humidity immediately prior to and/or during exposure of the spores to the chlorine dioxide gaseous sterilant. By enhancing the susceptibility of the spores to the sterilant, one may advantageously employ lower concentrations of chlorine dioxide gas and/or shorter exposure times than would be required if the foregoing humidification procedure were not employed. The relative humidity of the gaseous atmosphere employed in accordance with the humidification procedure of this invention will, of course, be substantially higher (e.g., 10%-15% higher) than the ambient humidity conditions to which the desiccated spores were exposed prior to sterilization.

In a preferred embodiment of the humidification procedure of this invention, desiccated spores are briefly humidified by exposure to highly humid air having a relative humidity of above about 60%, e.g., 70% to about 95% for at least about 15 minutes, and preferably for about 20 minutes to about one or more hours, immediately prior to the step of exposing the spores to the gaseous sterilant. Humidification may be conducted at about room temperature, although lower or higher temperatures (e.g. 25°-30° C.) may be employed if desired. It should be noted that although humidification is preferably conducted with humid air, other humid gases, such as humidified nitrogen, etc., may be employed.

The concentration of chlorine dioxide gas employed in conjunction with the foregoing humidification procedure preferably ranges from about 10 mg/L to about 40 mg/L. The article undergoing sterilization is preferably exposed to the gaseous sterilant for at least about 1 to about 4 hours. Moreover, as described in greater detail below, when humidification is conducted in a closed exposure chamber, the chlorine dioxide gas may be introduced into the chamber while it still contains the humid air employed during the humidification procedure.

The humidification procedure may be carried out using conventional apparatus. For example, the article contaminated with spores and/or live bacteria may be placed in a closed chamber and a vacuum drawn on the chamber. Water may then be injected into the evacuated chamber and vaporized to provide the desired humidity level in the chamber. After the spore contaminated article has been exposed to the humid atmosphere provided in the chamber for at least about 15 minutes, the chlorine dioxide sterilant gas is introduced into the humidified atmosphere of the chamber. The bacterially contaminated material is exposed to a gaseous environment of the gaseous sterilant for a period sufficient to sterilize the materials being treated, e.g., for about 30 minutes to about 24 hours, and preferably about 1 hour to about 3 hours.

In further embodiments of the humidification procedure of this invention, a stream of moist air and a separate stream of chlorine dioxide in an inert carrier gas may be introduced at the same time into an exposure chamber containing the spore-contaminated article. Alternatively, chlorine dioxide in an inert gas carrier may be mixed with water vapor or moist air, and the humid gaseous chlorine dioxide mixture introduced into the exposure chamber to sterilize the spore-contaminated article. Sterilization with the humid gaseous chlorine dioxide mixture is preferably conducted at about room temperature to about 30° C., and the relative humidity of the gaseous chlorine dioxide is preferably above about 60%, and most preferably about 70-95% RH. The contaminated article is preferably contacted with the humid sterilant for about 1 hour to about 4 hours, although longer exposure times may be employed if desired.

For commerical applications, it is desirable to employ a relatively narrow range of exposure times and gaseous chlorine dioxide concentrations to obtain about a 100% confidence level that the article has been sterilized— without the need to adjust exposure times and/or chlorine dioxide concentrations on the basis of the ambient humidity conditions to which the article has been exposed prior to sterilization. The humidification procedure disclosed herein aids in standardizing the susceptibility of spores to sterilization. This facilitates commercial usage of a narrow range of chlorine dioxide concentrations and a narrow range of exposure times to reproducibly sterilize articles, without regard to the ambient humidity conditions to which the spores contaminating the article have been exposed prior to sterilization.

Light catalyzes the decomposition of chlorine dioxide to chlorine and oxygen, and possibly other species. The oxygen and chlorine decomposition species of chlorine dioxide are far less effective sterilants than chlorine dioxide itself. In addition, chlorine is a corrosive substance which is incompatible with rubbers, plastics, and other materials which may be sterilized in accordance with this invention. By conducting the sterilization process of this invention in the dark or in very subdued light, the potential reduction in efficacy of the gaseous sterilant due to decomposition of the chlorine dioxide into less effective species as well as the disadvantages associated with the corrosive properties of chlorine are minimized.

The process disclosed in this application may be employed to sterilize a wide variety of microbiologically contaminated articles. In particular, the process of this invention may be employed to sterilize articles formed from glass, cellulosics, plastics, or the like which provide an essentially moisture-free substrate (e.g., a substrate with a less than about 10% moisture content or a substrate having some desiccated spores) for bacterial growth under ambient conditions. For example, medical or dental or other articles formed from any one or more of the following commonly employed materials may be sterilized in accordance with the process of this application: aluminum, aluminum oxide, chromed brass, cotton, gauzes (or cellulosics), copper, polyesters, ethylene vinyl acetate, latex, "Mylar", "Neoprene", nickel plated cold formed steel, "Nylon", platinum, polycarbonates, polyethylene, polymethylmethacrylate, polypropylene, styrene, Teflon, polyurethane, polyvinylalcohol, polyvinylacetate, polyvinyl chloride, pyrolytic and vitreous carbons, silicones, stainless steels, sterling silver, titanium, tungsten carbide, "Tygon", glass, ceramics, etc.

The sterilization process of this invention may also be employed to sterilize articles contained in packaging which is permeable to gaseous chlorine dioxide, and preferably packaging which is also permeable to moisture. For example, this process may be employed to sterilize medical or dental implements which have been packaged in gas permeable packaging under non-sterile conditions. A wide variety of conventional packaging materials are readily permeated by chlorine dioxide gas, including coated and uncoated paper, plastic sheeting, etc.

The chlorine dioxide gas may be prepared by any of the methods known in the art. A preferred method involves passing a stream of air diluted chlorine gas or nitrogen diluted chlorine gas at a metered rate through a column of finely divided sodium chlorite, and into a partially evacuated chamber. That procedure is disclosed in H. Grubitsch, E. Suppan, Monatsh., Vol. 93, p. 246 (1962), which is incorporated herein by reference.

A second suitable method for generating chlorine dioxide gas is the reaction of sodium chlorite solutions in the presence of acids. In one embodiment of this method a dilute solution of aqueous potassium persulfate is treated with a dilute solution of aqueous sodium chlorite at ambient temperatures, i.e., at 20°-30° C., in a closed reaction vessel. See Rosenblatt et al., *J. Org. Chem.*, 28, 2790 (1963). The temperature of the chloride dioxide atmosphere which forms in the space above the stirred reaction may be adjusted by external heating or cooling.

The desired amount of chlorine dioxide gas is admitted into a suitable exposure chamber which preferably has been partially evacuated, and which contains the objects to be sterilized. The chlorine dioxide gas is admitted into the exposure chamber in admixture with a carrier gas which is inert to (i.e. nonreactive with) chlorine dioxide at the concentrations which are used for sterilization. The final internal pressure may be adjusted, i.e., to near one atmosphere, with nitrogen, argon or another inert gas. At the end of the exposure period, the exposure chamber is evacuated to remove the chlorine dioxide and flushed with filtered inert gas or air. The evacuated chlorine dioxide may be easily destroyed by passing it through a reducing agent, for example, by passing it through a column of sodium thiosulfate chips.

The composition of the chlorine dioxide atmosphere employed for various sterilization runs may be determined colorimetrically by any of the standard methods, for example by the method of Wheeler, et al., *Microchem. J.*, 23, p. 160, (1978). A sample of the atmosphere inside the exposure chamber is obtained via a septum port using a gas-tight syringe. The volume of the sample is varied depending on the anticipated concentration of chlorine dioxide in the atmosphere. The atmosphere is preferably monitored at the beginning, and at the end of the exposure period. The syringe contents are injected into a suitable container, i.e., a cuvette, holding an appropriate volume of chemicals which react to result in a chlorine dioxide concentration-dependent color. After completion of the reaction, the absorbance of the solution at an appropriate wavelength is measured and the concentration of chlorine dioxide determined via a reference curve. The method may generally be adapted to employ any of the well known colorimetric methods of analyzing for chlorine dioxide.

The spores of the standard test organism employed to determine the effective sterilizing concentration of chlorine dioxide gas in certain of the specific examples set forth below were those of *Bacillus subtilis* var. *niger* (ATCC 9372). The dry spores of this organism are known to be extremely resistant to sterilization and have been often used to measure the effectiveness of gaseous sterilizing agents. See, e.g. P. M. Borick and R. E. Pepper, *The Spore Problem*, in *Disinfection*, M. A. Benarde, Ed., Marcel Decker, Publ., N.Y. (1970) at pages 85–102 and A. M. Cook and M. R. W. Brown, *J. Appl. Bact.*, 28, 361 (1965), the disclosures of which are incorporated herein by reference. Therefore, a given concentration of chlorine dioxide may be rated effective as a sterilizing agent if an initial population of $10^5$–$10^7$ spores showed no growth on the nutrient medium after nine days observation following exposure to said concentration.

In the detailed Examples which follow, standard suspensions of spores of *B. subtilis* var. *niger* were prepared as described by Dadd and Daley in *J. Appl. Bac-*

*teriol.*, 49, 89 (1980), which is incorporated herein by reference. Test paper strips for incubation were prepared by adding 0.2 ml of a methanolic suspension of the spores to 7×35 mm strips of presterilized Whatman 3 mm paper in glass Petri dishes. The papers were vacuum-dried (30 min. at 30° C. and 28 in. Hg) and kept at ambient temperature and humidity (20°-30° C., 40–60% relative humidity) prior to use. The spore load on each strip prepared in this way was approximately $1.4 \times 10^6$ spores.

Metal foil test pieces were prepared by fashioning 18×28 mm square aluminum foil into small cups. These were sterilized in glass Petri dishes. To each cup was added 0.2 ml of a methanolic suspension of the spores. The cups were dried at ambient temperature and held at ambient temperature and humidity prior to use. The spore load on each cup was approximately $1.4 \times 10^6$ spores.

The practice of the invention will be further illustrated by reference to the following detailed examples.

EXAMPLE 1

A 1000 ml 2-necked round-bottomed flask was equipped with a dropping funnel and magnetic stirring. A inlet tube for nitrogen gas equipped with a glass wool filter and a needle valve was positioned so that nitrogen could be admitted below the surface of the reaction mixture. An outlet tube was equipped with a needle valve and positioned so that gas could be allowed to pass from the top of the reaction vessel into the exposure vessel.

A 2000 ml glass reaction kettle equipped with a septum-capped port, a manometer, and inlet and outlet ports was employed as the exposure vessel. The outlet tube of the 1000 ml flask was connected to the inlet port of the exposure vessel.

In a typical run the 1000 ml flask was charged with 100 ml of an 8% aqueous sodium chlorite solution under nitrogen. All of the valves were closed and a solution of 2.0 g potassium persulfate in 100 ml of water was added dropwise with stirring. The reaction mixture was stirred for 30–45 minutes at 27° C. to complete the generation of the chlorine dioxide gas. The relative humidity of the chlorine dioxide gas generated by the foregoing procedure was about 60%.

The exposure chamber was loaded with 3-6 spore-coated paper strips or aluminum foil cups, each contained in an individual glass Petri dish. The spore-coated paper strips and aluminum foil cups were prepared from methanolic suspensions of spores of *B. subtilis*, in the manner described on page 11. It has been reported in the literature that exposure to methanol may enhance the sensitivity of the spores to chemosterilization. The chamber was swept with nitrogen, closed and then evacuated (approx. 28 in. Hg). The outlet valve on the tube leading from the reaction vessel was opened, and the amount of chlorine dioxide gas admitted from the reaction vessel was controlled by following the increased pressure readings on the manometer. The outlet valve was closed and the pressure in the exposure vessel was then brought to one atmosphere by admission of nitrogen.

The atmosphere in the exposure vessel was immediately sampled by removal of 0.5–2.0 ml of the atmosphere by means of a gas-tight syringe via the septum. The chlorine dioxide concentration was determined by the method of Wheeler, et al., *Microchem. J.*, 23, 160 (1978). After 60 minutes had elapsed the atmosphere was sampled again. The exposure chamber was then evacuated and refilled with filtered air. The evacuation and refilling steps were repeated, the chamber was opened and the contents removed under sterile conditions.

The paper strips were aseptically transferred to individual tubes of trypticase soy broth and incubated at 37° C. Observations to determine the presence or absence of spore growth were made after 24 and 48 hours. Those tubes which did not show growth after 48 hours were incubated for one week and observed every 24 hours. If no growth was observed after one week, the strip was recorded as negative, or sterilized.

After exposure, the foils were transferred into individual tubes containing 20 ml of sterile water and a few glass beads. After vigorous shaking to dislodge and suspend the spores, 0.1 ml of the suspension was placed in duplicate on a plate of trypticase soy agar. The plates were incubated at 37° C. and observed as described above for the paper strips. Appropriate control strips and foils were run for these determinations. The outcome of 18 specific runs is summarized in Table I as Examples 2–19.

TABLE I
CHLORINE DIOXIDE STERILIZATION

| Example | Chlorine Dioxide (mg/L) | Results* Strips | Foil Cups |
|---|---|---|---|
| 2 | 11 | 0/6 | 0/6 |
| 3 | 12 | 0/6 | 0/6 |
| 4 | 25 | 0/6 | 0/6 |
| 5 | 31 | 1/6 | 0/6 |
| 6 | 34 | 0/6 | 5/6 |
| 7 | 35 | 1/6 | 0/6 |
| 8 | 40 | 0/6 | 0/6 |
| 9 | 41 | 0/6 | 0/6 |
| 10 | 44 | 0/5 | 0/6 |
| 11 | 45 | 0/6 | 0/6 |
| 12 | 46 | 0/6 | 0/6 |
| 13 | 65 | 0/6 | 0/6 |
| 14 | 69 | 1/6 | 0/6 |
| 15 | 78 | 0/6 | 0/6 |
| 16 | 84 | 0/6 | 0/6 |
| 17 | 94 | 0/6 | 0/6 |
| 18 | 98 | 0/6 | 0/6 |
| 19 | 113 | 0/6 | 0/6 |

*Exposure time - 1 hr. Results in number of strips or cups on which growth is observed/number of strips or cups exposed.

The results of Examples 2–19 demonstrate that a chlorine dioxide concentration of at least 40 mg/L was effective to sterilize paper strips contaminated with dry *B. subtilis* spores, and thus, presumably, to kill any other microorganisms present. The scattered incidences of growth observed in Examples 5, 7 and 14 may be largely discounted as due to random experimental error. It is expected that more rigorous control of the laboratory procedures of the biological standards would demonstrate effective sterilization over the complete range of gas concentrations employed. Similar concentrations would be expected to sterilize other types of porous organic surfaces, such as rubber, gas permeable plastic, sponge, plant material, wood and the like, without causing appreciable decomposition or residue deposition.

A concentration of chlorine dioxide of at least 35 mg/L was adequate to sterilize aluminum foil contaminated with dry spores. The growth observed on foil in Example 6 was probably due to a ramdom experimental error, since a range of lower gas concentrations consistently resulted in sterilization. These results led to the expectation that other nonporous surfaces normally impermeable to gas sterilizing agents would be readily sterilized under similar conditions, such as those of medical or dental instruments or implements formed from metals such as stainless steels, plated steel, aluminum and nickel or from nonporous plastics, porcelain, ceramics, or glass.

Chlorine dioxide gas has also been successfully employed to sterilize commercially-available spore strips which are sealed in gas permeable paper envelopes. A procedure which may be used to sterilize such materials is described below.

EXAMPLE 20

Six Spordi ® paper spore strips (American Sterilizer Corp., Erie, Pa.), each containing a mixture of spores of *B. subtilis* and *B. stearothermophilus* (NCTC 10003) and each enclosed in a sealed, sterile envelope of glassine paper are exposed to atmospheres containing 50 and 100 mg/L of chlorine dioxide gas as described in Example 1. The sealed spore strips are removed from the exposure chamber, opened under sterile conditions and incubated as described in Example 1. Growth levels are observed after nine days of incubation which indicate that the strips are effectively sterilized under these conditions.

It is, therefore, expected that chlorine dioxide will effectively sterilize contaminated surfaces which are sealed in gas permeable container materials such as coated and uncoated paper, plastic sheeting, and the like without significantly reacting with the container materials. The ability of effective concentrations of chlorine dioxide to readily permeate such enclosures would find application in the sterilization of medical products which are preferably sterilized after packaging so as to be maintained in a sterile condition during shipping and storage.

EXAMPLE 21

In this experiment 72 Spordi ® paper spore strips (American Sterilizer Corp., Erie, Pa.) were employed. Each strip was enclosed in a glassine envelope, and the strips were contaminated with a mixture of spores of *B. subtillis* and *B. stearothermphilus* (NCTC 10003). The strips in their glassine envelopes were equally divided into three sets—Set I was stored in the normal laboratory atmosphere, Set II was placed in a chamber at a controlled relative humidity of 33%, while Set III was placed in a desiccator over Drierite. The strips were permitted to equilibrate with their environment for three days. Upon conclusion of the storage period, the strips in Sets I, II and III were equally divided into two Groups A and B, and then exposed to chlorine dioxide in the darkened interior of an exposure chamber in the manner described below.

The strips in Group A were exposed to high humidity conditions in the exposure chamber at about 27° C. Humidification was performed by drawing a vacuum of about 27 in. Hg on the two-liter exposure chamber, and then injecting about 0.1 ml of distilled water into the evacuated chamber. The relative humidity in the exposure chamber was above about 70%. The strips in Group A were exposed to the humid conditions in the chamber for about 20 minutes. Chlorine dioxide, at the desired concentration level, was introduced into the chamber without prior evacuation of the moist air from the chamber. The strips were exposed to the chlorine dioxide at about 27° C. for about 2 hours.

The strips in Group B were exposed to chlorine dioxide in the same manner as those in Group A, with the exception that the strips in Group B were not subjected to the preliminary humidification procedure described above with respect to the strips in Group A. The relative humidity of the chlorine dioxide/carrier gas employed to treat Group B ws less than about 10%. The chlorine dioxide employed to treat both the strips in Group A and Group B was generated by passage of chlorine gas through finely divided dry sodium chlorite.

After sterilization the spore strips were removed from the exposure chamber under sterile conditions, and incubated in the manner described in Example 1. The results are summarized in Table II, in terms of the number of strips in which bacterial growth was observed/number of strips treated.

TABLE II

| mg/L, $ClO_2$ | Set I (normal) | Set II (33% RH) | Set III (desiccator) |
|---|---|---|---|
| Group A - (humidification) | | | |
| 33.6 | 0/4 | 0/4 | 0/4 |
| 29.0 | 0/4 | 0/4 | 0/4 |
| 9.1 | 3/4 | 2/4 | 3/4 |
| Group B - (non-humidification) | | | |
| 61.7 | 4/4 | 0/4 | 4/4 |
| 59.9 | 4/4 | 0/4 | 4/4 |
| 38.1 | 1/4 | 0/4 | 4/4 |

Table II illustrates that the humidified spores in Group A were sterilized by the action of the chlorine dioxide gas at concentrations of about 29 mg/L and above. In contrast, the spores in Group B (Sets I and III) which were treated with a dry chlorine dioxide gas and not humidified prior to application of the sterilant, were far more resistant to the chlorine dioxide gas. The bacterial growth noted with respect to the strips in Group B (Set I) is attributed to the low humidity conditions in the laboratory (estimated to be about 15% RH) to which the strips were exposed prior to sterilization, coupled with the fact that the strips were treated with a dry chlorine dioxide sterilant (less than about 10% RH).

Table III presents data on *B. subtilis* contaminated paper strips and aluminum foil cups. The foil cups and paper strips were contaminated in the manner described above on page 11, except that an aqueous spore suspension was employed as the contaminant. The spore-contaminated paper strips and foil cups were exposed to the various concentrations of chlorine dioxide specified in Table III in the darkened interior of the exposure chamber. The exposure time was two hours. No control over humidity conditions was exercised. In this trial the chlorine dioxide gas was generated in a dry form by passage of chlorine through a column of dry finely divided sodium chlorite. In additon, the foil cups and paper strips were dry and maintained for several days at room temperature and relatively low ambient humidity conditions (less than about 15% RH). Accordingly, the apparent resistance of the spores to the sterilant as shown by Table III is believed to be due to the combination of the use of a dry sterilant gas to treat spores which were in a relatively desiccated form, and, hence resistant to sterilization.

TABLE III

TEST RESULTS - GRADED SPORE LOADS*

Foil Cups

| ClO$_2$ mg/L | 10$^{6*}$ | 10$^5$ | 10$^4$ | 10$^3$ | 10$^2$ |
|---|---|---|---|---|---|
| | | Spore Load | | | |
| 50.8 | 4/4** | 4/4 | 4/4 | 0/4 | 0/4 |
| 36.3 | 4/4 | 2/4 | 4/4 | 0/4 | 0/4 |
| 23.4 | 4/4 | 0/4 | 0/4 | 0/4 | 0/4 |
| 19.1 | 4/4 | 4/4 | 2/4 | 3/4 | 1/4 |
| 14.5 | 4/4 | 3/4 | 4/4 | 1/4 | 0/4 |
| 12.7 | 4/4 | 4/4 | 4/4 | 0/4 | 1/4 |
| 7.3 | 4/4 | 3/4 | 4/4 | 4/4 | 0/4 |
| 5.8 | 4/4 | 4/4 | 4/4 | 4/4 | 3/4 |
| 4.4 | 4/4 | 4/4 | 4/4 | 4/4 | 4/4 |
| | | Paper Strips | | | |
| 50.8 | 4/4 | 4/4 | 0/4 | 0/4 | 0/4 |
| 36.3 | 4/4 | 4/4 | 0/4 | 0/4 | 0/4 |
| 23.4 | 4/4 | 2/4 | 1/4 | 0/4 | 0/4 |
| 19.1 | 4/4 | 4/4 | 2/4 | 0/4 | 0/4 |
| 14.5 | 4/4 | 4/4 | 1/4 | 0/4 | 0/4 |
| 12.7 | 4/4 | 3/4 | 0/4 | 0/4 | 0/4 |
| 7.3 | 4/4 | 4/4 | 3/4 | 0/4 | 0/4 |
| 5.8 | 4/4 | 4/4 | 0/4 | 1/4 | 0/4 |
| 4.4 | 4/4 | 4/4 | 2/4 | 0/4 | 0/4 |

*Pre-sterilization number of spores on the contaminated article.
**number grew/number exposed.

EXAMPLE 22

390 glass cups coated with spores of *B. subtilis* were equally divided into Groups A and B. Group A was exposed to chlorine dioxide generated by the dry method described in Example 21, without any control over humidity conditions. The contaminated glass cups in Group B were humidified and then exposed to the chlorine dioxide gas in accordance with the procedure of Example 21. Both Groups A and B were exposed to the gaseous sterilant in a closed and darkened chamber for about 2 hours. The data is given in Table IV, wherein the numbers with superscripts (10$^6$, etc.) indicate the pre-sterilization number of spores per cup, while the numbers given in the body of Table IV represent the number of glass cups out of the 6 cups sterilized that produced live bacteria upon culturing subsequent to sterilization.

TABLE IV

| ClO$_2$ mg/L | 10$^6$ | 10$^5$ | 10$^4$ | 10$^3$ | 10$^2$ |
|---|---|---|---|---|---|
| | | Group A NO PRE-HUMIDIFICATION | | | |
| 114/3 | 6/6* | 6/6 | 3/6 | 0/6 | 0/6 |
| 74.4 | 6/6 | 6/6 | 6/6 | 5/6 | 0/6 |
| 61.7 | 6/6 | 6/6 | 4/6 | 3/6 | 1/6 |
| 45/4 | 6/6 | 6/6 | 6/6 | 5/6 | 0/6 |
| 29.0 | 6/6 | 6/6 | 6/6 | 5/6 | 1/6 |
| 24.6 | 6/6 | 6/6 | 6/6 | 6/6 | 4/6 |
| 8.2 | 6/6 | 6/6 | 6/6 | 6/6 | 6/6 |
| 3.6 | 6/6 | 6/6 | 6/6 | 6/6 | 6/6 |
| | | Group B PRE-HUMIDIFIED | | | |
| 119.7 | 0/6 | 0/6 | 0/6 | 0/6 | 0/6 |
| 47.2 | 0/6 | 0/6 | 0/6 | 0/6 | 0/6 |
| 30.8 | 0/6 | 0/6 | 0/6 | 0/6 | 0/6 |
| 6.3 | 0/6 | 0/6 | 0/6 | 0/6 | 0/6 |
| 4.0 | 0/6 | 0/6 | 0/6 | 0/6 | 0/6 |

*Number grew/number exposed; sterilization conducted at 27° C.

EXAMPLE 23

In this experiment, the test items were prepared by placing 0.1 ml of an aqueous suspension of *B. subtilis* var. *niger* spores in small glass cups (9 mm × 14 mm). The cups were vacuum dried for 2 hours in sterile Petri plates each containing 6 test cups. Each test cup carried a spore load of approximately 1 × 10$^6$ spores. The chlorine dioxide used for sterilizing was prepared by passing chlorine through dry sodium chlorite. Test cups were sterilized at the temperatures, exposure times and humidities shown in the following tables.

TABLE V

30 MINUTE EXPOSURE TO CHLORINE DIOXIDE GAS*

| ClO$_2$ | Temperature | |
|---|---|---|
| mg/L | 27° C. | 37° C. |
| 20 | 0/6** | |
| 17 | | 6/6 |
| 12 | 3/6 | |
| 10 | 6/6 | |
| 7 | | 6/6 |
| 6 | 4/5, 6/6 | |
| 5 | 3/6 | 6/6 |
| 4 | 2/6 | |
| 3 | | 6/6 |

*Chamber and contents humidified with 0.1 ml water at 27 in. Hg vacuum for 20 minutes prior to introduction of chlorine dioxide at stated concentration into the chamber. The relative humidity in the chamber was about 80%.
**Values given as number of cups showing growth/number of cups exposed.

TABLE VI

60 MINUTE EXPOSURE TO CHLORINE DIOXIDE GAS*

| ClO$_2$ | Temperature | | |
|---|---|---|---|
| mg/L | 15° C. | 27° C. | 37° C. |
| 32 | | | 5/6** |
| 27 | 2/6 | | |
| 23 | | | 3/6 |
| 22 | | 1/6 | |
| 21 | | 1/6 | |
| 19 | 3/6 | | 1/6 |
| 18 | 2/6 | | 5/6 |
| 17 | | 1/6 | |
| 16 | | 0/6 | |
| 15 | | | 6/6 |
| 14 | | | 6/6 |
| 11 | | | 6/8 |
| 6 | | 0/6 | 5/6 |
| 5 | | | 4/6 |
| 2 | 1/6 | 4/5 | |
| 1 | 3/6 | 3/6 | 5/6,6/6 |

*Chamber and contents humidified with 0.1 ml water at 27 in. Hg vacuum for 20 minutes prior to introduction of chlorine dioxide gas into the chamber. The relative humidity in the chamber was about-80%.
**Values given as number of cups showing growth/number of cups exposed.

TABLE VIII

120 MINUTE EXPOSURE TO CHLORINE DIOXIDE GAS*

| ClO$_2$ | Temperature | | | |
|---|---|---|---|---|
| mg/L | 15° C. | 27° C. | 37° C. | 37° C.** |
| 67 | 2/12*** | | | |
| 51 | | | | 0/6,0/6 |
| 47 | 0/12 | | | |
| 44 | 6/12 | | | |
| 39 | | 0/6 | | |
| 31 | | | 6/12 | |
| 30 | | | 1/12 | |
| 21 | | | 9/12 | |
| 20 | | 0/6 | | |
| 19 | 0/12 | 6/6**** | | |
| 18 | 7/12 | | | |
| 17 | 10/12 | | | |
| 16 | | | | 6/6,0/6 |
| 15 | 1/12 | 0/12,0/12, 0/12 | 2/12 | |
| 14 | | | 7/12 | |
| 13 | | | | 6/6,2/6 |
| 12 | 10/12 | | | |
| 10 | | 0/6 | 8/12 | |

TABLE VIII-continued

| ClO₂ mg/L | 120 MINUTE EXPOSURE TO CHLORINE DIOXIDE GAS* Temperature | | | |
|---|---|---|---|---|
| | 15° C. | 27° C. | 37° C. | 37° C.** |
| 9 | 9/12 | | | |
| 8 | | 2/12, 0/12, 0/12 | 12/12 | 0/6, 0/6 |
| 7 | 5/12 | | | |
| 6 | | | | 0/6, 0/6 |
| 5 | | 0/7 | | |
| 3 | | | 10/12, 12/12, | |
| 2 | | | 12/12 | |
| 1 | 12/12 | | | |
| 0.5 | | | 12/12 | |
| 0.2 | 11/12 | | | |

*Chamber and contents humidified with 0.1 ml water at 27 in. Hg vacuum for 20 minutes prior to introduction of the chlorine dioxide gas. The relative humidity of the chamber was about 80%.
**Humidification with 0.2 ml of wtaer at 27 in. Hg vacuum for 60 minutes, RH was about 90%.
***Values given as number of cups showing growth/number of cups exposed.
****Data believed to be due to experimental error.

The data presented above indicates that under the humidification procedures employed, optimum sterilization was obtained at sterilization temperatures of 27° C. with exposure times of two hours. Although bacterial growth was noted during the trials conducted at 15° C. and 37° C., it is believed that sterilization could be achieved at those temperatures by extending the chlorine dioxide exposure time. The data presented also indicates that chemosterilization by chlorine dioxide is not enhanced either by conducting the process at temperatures above (37° C.) or below (15° C.) about room temperature (e.g. 20°–30° C.).

EXAMPLE 24

A dry mixture of nitrogen and chlorine dioxide gas suitable for use as a gaseous chemosterilant is prepared as follows:

Chlorine gas from a standard cylinder fitted with a needle valve regulator is introduced slowly by means of a tee into a stream of nitrogen. The stream of nitrogen diluted chlorine is then passed over finely divided sodium chlorite contained in a series of three columns. The first two glass columns consist of gas drying bottles packed with sodium chlorite to provide columns measuring $3.5 \times 14$ cm. The third column in the series consists of a glass tube packed to provide a column measuring $1 \times 40$ cm. The gas exiting the last column may be introduced directly into an evacuated exposure chamber (e.g. approx. 27 in. Hg), or into an evacuated flask for later use.

While certain representative embodiments of the present invention have been discussed herein for the purpose of illustrating the present invention, it will be appreciated by those of ordinary skill in this art that modifications thereof may be made without departing from the scope and spirit of the present invention.

What is claimed is:

1. A method for sterilizing the surface of an article wherein the surface is at least substantially gas impermeable and said surface is contaminated with bacterial spores comprising the steps of exposing the spores on said surface to a humid gaseous atmosphere effective to enhance the susceptibility of said spores to subsequent chemosterilization with chlorine dioxide gas, and then exposing said spores present on said surface to an amount of gaseous chlorine dioxide in an inert carrier gas effective to sterilize said surface by killing the spores.

2. The method according to claim 1 wherein said humid gaseous atmosphere is comprised of humid air.

3. The method according to claim 2 wherein said humid gaseous atmosphere is comprised of humid air which is at a temperature within the range of about room temperature to about 30° C., and wherein the relative humidity of said humid air is above 60%.

4. The method according to claim 2 wherein said surface is exposed to said humid air for at least about 15 minutes, and immediately thereafter said spores are exposed to said gaseous chlorine dioxide for a time sufficient to sterilize said surface.

5. The method according to claims 1, 2, 3 or 4 wherein the concentration of chlorine dioxide in said inert carrier gas is at least 10 mg/L.

6. The method according to claim 3 wherein said spores are spores of *B. subtilis* var. *niger*.

7. The method according to claim 3 wherein said gaseous chlorine dioxide employed to sterilize said surface is prepared by passing chlorine through dry sodium chlorite; the concentration of said chlorine dioxide in said inert carrier gas is about 10 to about 40 mg/L; and wherein said relative humidity is at least 70%.

8. The method according to claim 3 wherein said chlorine dioxide employed to sterilize said surface is prepared by reacting aqueous sodium chlorite with a persulfate compound.

9. The method according to claim 3 wherein immediately prior to exposure to said humid atmosphere said spores on said surface were exposed to an ambient relative humidity of less than 30%.

10. The method according to claim 3 wherein said relative humidity is about 70%–95%, and said spores which contaminate said surface are in a desiccated state.

11. The method according to claim 5 wherein spores are exposed to said chlorine dioxide gas for at least about two hours.

12. The method according to claim 1 or 3 wherein said surfaces comprise the surface of an article and wherein during sterilization said article is contained in a material which is permeable to moisture and chlorine dioxide gas.

13. The method according to claims 1, 3 or 7 wherein said spores are exposed to said gaseous chlorine dioxide in the dark or subdued light.

14. The method according to claim 11 wherein said chlorine dioxide gas is at a temperature of about 27° C.

15. The method according to claim 11 wherein said surface comprises the gas impermeable surface of a medical or a dental implement.

16. A method for sterilizing the surface of a bacterial spore-contaminated article, wherein the contaminated surface is at least substantially gas impermeable and said surface is contaminated with bacterial spores, which comprises:
  (a) placing said article in an exposure chamber, and in said chamber,
  (b) providing a humid gaseous atmosphere in contact with said spores sufficient to enhance the susceptibility of the spores contaminating said article to chemosterilization with gaseous chlorine dioxide, and
  (c) introducing an amount of chlorine dioxide gas into said chamber effective to sterilize said article by killing the spores.

17. The method according to claim 16 wherein said humid gaseous atmosphere is comprised of humid air which is heated in said chamber to above about room temperature to about 30° C., and wherein the relative humidity of said air is above 60%.

18. The method according to claim 17 wherein said relative humidity is about 70% to about 95%, and wherein immediately prior to being placed in said chamber said spores were exposed to an ambient relative humidity of less than 30%.

19. The method according to claim 17 wherein said chlorine dioxide comprises a gaseous mixture of chlorine dioxide in an inert carrier gas wherein the concentration of chlorine dioxide is at least 10 mg/L.

20. The method according to claim 19 wherein said chlorine dioxide employed to sterilize said article is prepared by passing chlorine through dry sodium chlorite.

21. The method according to claim 19 wherein said chlorine dioxide gas is at a temperature of about room temperature to about 30° C.

22. The method according to claim 21 wherein said surface is comprised of metal, glass, porcelain, rubber or plastic; and wherein said spores are in a desiccated state.

23. The method according to claim 17 wherein said humid air is provided by exposing water in said chamber to sub-atmospheric pressures sufficient to vaporize water.

24. The method according to claim 19 wherein said spores are spores of *B. subtilis* var. *niger.*

25. The method according to claim 17 wherein during sterilization said article is contained in a moisture and chlorine dioxide gas permeable material.

26. The method according to claim 21 wherein said chlorine dioxide gas is at a temperature of about 27° C.

27. The method according to claim 21 or 26 wherein said surface is exposed to said chlorine dioxide gas for at least about two hours.

28. The method according to claim 19 wherein the inert carrier gas is nitrogen.

29. The method according to claim 19 wherein said surface is exposed to chlorine dioxide in the dark or subdued light.

30. A method for sterilizing an article which includes a bacterial spore-contaminated surface wherein the surface is at least substantially gas impermeable comprising exposing said surface to a gaseous atmosphere comprised of chlorine dioxide gas and water vapor, wherein the amount of water vapor in said atmosphere is adapted to enhance the susceptibility of said spores to the sporicidal action of said chlorine dioxide, and wherein said exposure to said gaseous atmosphere is effective to sterilize said surface by killing the spores thereon.

31. The method according to claim 30 wherein said gaseous atmosphere is prepared by admixing humid air and a previously prepared mixture of chlorine dioxide in an inert carrier gas.

32. The method according to claim 31 wherein said inert carrier gas is nitrogen.

33. The method according to claim 30 wherein said gaseous sterilant is comprised of a mixture of chlorine dioxide, water vapor and an inert carrier gas.

34. The method according to claim 33 wherein said inert carrier gas is nitrogen.

35. The method according to claim 33 wherein the concentration of chlorine dioxide in said mixture is at least 10 mg/L.

36. The method according to claim 31 or 33 wherein said gaseous atmosphere is at a temperature of about room temperature to about 30° C., and wherein the relative humidity of said atmosphere is at least 60%.

37. The method according to claim 36 wherein said spores are spores of *B. subtilis* var. *niger.*

38. The method according to claim 30 wherein said article is a medical or dental implement.

39. The method according to claim 30 wherein said surface is exposed to said atmosphere in the dark or subdued light.

40. The method according to claim 30 wherein during sterilization said article is contained in a material which is permeable to moisture and chlorine dioxide gas.

41. The method according to claim 30, 31 or 33 wherein immediately prior to sterilization said spores were exposed to an ambient relative humidity of below about 30%.

42. The method according to claim 31 or claim 33 wherein the chlorine dioxide in said mixture was prepared by passing chlorine gas through dry sodium chlorite.

43. A method for sterilizing a surface which is at least substantially gas impermeable and contaminated with desiccated spores comprising the steps of exposing the spores on said surface to a humid gaseous atmosphere to enhance the susceptibility of said spores to subseqent chemosterilization and then exposing said spores to an amount of gaseous chlorine dioxide in an inert carrier gas effective to sterilize said desiccated spores on said surface by killing the spores.

44. A method for sterilizing an article which includes a surface which is at least substantially gas impermeable and contaminated with desiccated spores which comprises exposing said surface to a gaseous atmosphere comprised of chlorine dioxide gas and water vapor, wherein the amount of water vapor in said atmosphere is adapted to enhance the susceptibility of said spores to the sporicidal action of said chlorine dioxide, and thereby to sterilize the surface by killing the spores thereon.

45. A method for chemosterilizing the surface of an article wherein the surface is at least substantially gas impermeable and the surface is contaminated with bacterial spores which are in a low moisture or desiccated state, which comprises the steps of exposing said spores to water vapor to enhance the susceptibility of the spores on said surface to chemosterilization with gaseous chlorine dioxide, and exposing said spores on said surface to an amount of gaseous chlorine dioxide effective to sterilize said spore-contaminated surface by killing the spores thereon.

46. The method according to claim 45 wherein said surface is comprised of glass, cellulosic material or plastic.

47. The method according to claim 45 wherein said surface is a gas impermeable surface, and said sterilization is performed at a temperature which does not overly exceed ambient temperature, and said sterilization is conducted for a time period sufficient to kill the spores on said contaminated surfaces.

48. The method according to claim 47 wherein said chlorine dioxide gas is in an inert carrier gas, wherein the concentration of said chlorine dioxide is about 10 to about 40 mg/L.

49. The method according to claim 45 wherein said water vapor has a relative humidity which is above about 60%.

50. The method according to claim 45 wherein said surface is a surface of a medical or dental implement.

51. The method according to claim 49 wherein said surface is the surface of a medical or dental implement.

52. The method according to claim 48 wherein said surface is the surface of a medical or dental implement.

53. The method according to claim 2, wherein said surface is the surface of a medical or dental implement.

54. The method according to claim 53 wherein said surface is formed of a material selected from the group consisting of glass, plastics, ceramics, stainless steel, sterling silver, aluminum, aluminum oxide, pyrolytic or vitreous carbons, chromed brass, copper, platinum, and titanium.

55. The method according to claim 16, wherein said surface is formed of a material selected from the group consisting of glass, plastics, ceramics, stainless steel, sterling silver, aluminum, aluminum oxide, pyrolytic or vitreous carbons, chromed brass, copper, platinum, and titanium.

56. The method according to claim 30, wherein said surface is formed of a material selected from the group consisting of glass, plastics, ceramics, stainless steel, sterling silver, aluminum, aluminum oxide, pyrolytic or vitreous carbons, chromed brass, copper, platinum and titanium.

57. The method according to claim 43, wherein said surface is formed of a material selected from the group consisting of glass, plastics, ceramics, stainless steel, sterling silver, aluminum, aluminum oxide, pyrolytic or vitreous carbons, chromed brass, copper, platinum and titanium.

58. The method according to claim 44, wherein said surface is formed of a material selected from the group consisting of glass, plastics, ceramics, stainless steel, sterling silver, aluminum, aluminum oxide, pyrolytic or vitreous carbons, chromed brass, copper, platinum and titanium.

59. The method according to claim 45, wherein said surface is formed of a material selected from the group consisting of glass, plastics, ceramics, stainless steel, sterling silver, aluminum, aluminum oxide, pyrolytic or vitreous carbons, chromed brass, copper, platinum and titanium.

60. The method according to claims 1, 16, 30, 43, 44 or 45 wherein said surface is formed from a material selected from the group consisting of polyesters, ethylene vinyl acetate, latex, Neoprene, Nylon, polycarbonates, polyethylene, polymethylmethacrylate, polypropylene, styrene, Teflon, polyurethane, polyvinylalcohol, polyvinylacetate, Tygon, and polyvinylchloride.

* * * * *